US012784314B2

(12) United States Patent
Juergens et al.

(10) Patent No.: US 12,784,314 B2
(45) Date of Patent: Nov. 3, 2026

(54) METHOD AND APPARATUS FOR CORRECTING MATERIAL-INDUCED EFFECTS IN CT IMAGES

(71) Applicant: Siemens Healthineers AG, Forchheim (DE)

(72) Inventors: Markus Juergens, Adelsdorf (DE); Bernhard Schmidt, Fuerth (DE)

(73) Assignee: Siemens Healthineers AG, Forchheim (DE)

( * ) Notice: Subject to any disclaimer, the term of this patent is extended or adjusted under 35 U.S.C. 154(b) by 550 days.

(21) Appl. No.: 18/355,553

(22) Filed: Jul. 20, 2023

(65) Prior Publication Data

US 2024/0029326 A1 Jan. 25, 2024

(30) Foreign Application Priority Data

Jul. 21, 2022 (DE) .................... 10 2022 207 476.9

(51) Int. Cl.
*G06T 11/00* (2026.01)
*G06T 7/00* (2017.01)
*G06T 12/30* (2026.01)
*G16H 30/20* (2018.01)

(52) U.S. Cl.
CPC ............ *G06T 12/30* (2026.01); *G06T 7/0012* (2013.01); *G06T 2207/10081* (2013.01); *G06T 2207/30004* (2013.01); *G06T 2211/408* (2013.01); *G16H 30/20* (2018.01)

(58) Field of Classification Search
CPC ................ G06T 2207/10081; G06T 2211/408
See application file for complete search history.

(56) References Cited

U.S. PATENT DOCUMENTS

| | | | | |
|---|---|---|---|---|
| 8,355,555 B2 * | 1/2013 | Chen | G06T 5/50 | 382/131 |
| 9,036,879 B2 * | 5/2015 | Mendonca | A61B 6/032 | 378/4 |
| 2009/0086883 A1 * | 4/2009 | Harer | A61B 6/032 | 378/4 |
| 2010/0135453 A1 * | 6/2010 | Mendonca | A61B 6/032 | 378/5 |
| 2011/0064292 A1 * | 3/2011 | Chen | G06T 5/50 | 382/131 |

(Continued)

FOREIGN PATENT DOCUMENTS

| | | | |
|---|---|---|---|
| DE | 102009044683 A1 | 6/2010 | |
| DE | 102016203257 A1 | 8/2017 | |
| WO | WO-2016002084 A1 * | 1/2016 | G06T 12/20 |

*Primary Examiner* — Ted W Barnes
(74) *Attorney, Agent, or Firm* — Harness, Dickey & Pierce, P.L.C.

(57) ABSTRACT

A method for correcting material-induced effects in CT images, comprising: providing a CT scan dataset including CT scan data of an object at at least two different energies; calculating a plurality of first material density values for a first substance type from the CT scan data of the CT scan dataset; calculating a plurality of correction factors based on the plurality of first material density values, wherein each correction factor is assigned to a second material density value for a second substance type; and calculating CT images from the plurality of first and second material density values, wherein at least one of the CT images is corrected via the plurality of correction factors.

25 Claims, 3 Drawing Sheets

(56) References Cited

U.S. PATENT DOCUMENTS

| | | | | |
|---|---|---|---|---|
| 2012/0207270 | A1* | 8/2012 | Flohr | A61B 6/4014 378/5 |
| 2017/0086769 | A1* | 3/2017 | Allmendinger | A61B 6/032 |
| 2017/0245816 | A1 | 8/2017 | Flohr et al. | |
| 2018/0042565 | A1* | 2/2018 | Wilson | A61B 5/33 |
| 2020/0155007 | A1* | 5/2020 | Shapira | A61B 5/0073 |

* cited by examiner

METHOD AND APPARATUS FOR CORRECTING MATERIAL-INDUCED EFFECTS IN CT IMAGES

CROSS-REFERENCE TO RELATED APPLICATION(S)

The present application claims priority under 35 U.S.C. § 119 to German Patent Application No. 10 2022 207 476.9, filed Jul. 21, 2022, the entire contents of which are incorporated herein by reference.

FIELD

One or more example embodiments of the present invention relate to a method and an apparatus for correcting material-induced effects in CT images, in particular for correcting mass and/or volume effects on virtual non-calcium images derived from dual-energy CT data or photon-counting CT data.

BACKGROUND

Dual-energy CT (DECT) or photon-counting CT (PCCT) make it possible to break CT values down into specific pairs or triplets of material-specific CT values. These CT values can then provide information about the material composition of a body region, which has significant medical diagnostic value.

For example, DECT imaging can be used to calculate the local iodine uptake in a body region by separating the measurement results in respect of water (a model for the underlying blood/parenchyma) and iodine. This produces a virtual non-contrast (VNC) image and an iodine image, wherein the VNC is expected to show the physiological details without iodine. Such an approach is known as "base material decomposition". It works well when the iodine concentration is negligible compared to the density of water or of the underlying tissue.

A similar principle can be used to determine bone structure. In bone marrow, the three materials of interest are "yellow marrow" (fat, approx. −100 Hounsfield units, HU), "red marrow" (approx. 50 HU) and calcium (as a component of hydroxylapatite, "HA"). To separate these materials, an HA image and a VNCa (virtual non-calcium) image are calculated in a manner similar to the procedure described above, wherein the HA image shows hydroxylapatite and the VNCa shows the physiological details without hydroxylapatite. Using the CT values (in HU), yellow and red bone marrow can be identified in the VNCa image, or fluid retention (edema) resulting from e.g. an impact injury.

However, when calculating a VNCa image, a volume effect in respect of HA may reduce the CT value. If, for example, at a concentration of 200 mg/ml and a nominal density of 3.16 g/ml, hydroxylapatite were to account for 6% of the volume, assuming that the volumes of HA and bone marrow add up linearly, the density of the marrow components would be reduced to 94% of that of pure bone marrow without HA. In terms of CT numbers, this reduces the CT value of the VNCa from the original range of values (white bone marrow: −100 HU, red bone marrow: 50 HU) to −154 HU for white bone marrow and −13 HU for red bone marrow. This means that in the VNCa image the CT values are consistently shifted to lower CT values. However, such a shift is misleading for a viewer of the images, as red bone marrow is then shown at values lower than 0 HU, which is normally interpreted as fatty substance (yellow bone marrow).

In the existing prior art, volume effects are already taken into account and correction methods described, e.g. based on 3-material decomposition allowing for volume effects. However, these often rely on theoretical models and the assumption that the volume is maintained. The originally measured CT values, which basically constitute the only objective information about the body region, are not taken into account.

SUMMARY

To at least avoid the disadvantages described above, an object of example embodiments of the present invention is to provide an alternative, more convenient method and a corresponding apparatus for correcting volume effects. This correction shall be based on the measured CT values.

At least this object is achieved by a method according to one or more example embodiments of the present invention and/or as claimed in the claims, an apparatus according to one or more example embodiments of the present invention and/or as claimed in the claims, as well as by a diagnostic facility according to one or more example embodiments of the present invention and/or as claimed in the claims, a control facility according to one or more example embodiments of the present invention and/or as claimed in the claims, and a CT system according to one or more example embodiments of the present invention and/or as claimed in the claims.

A method according to an embodiment of the present invention for correcting material-induced effects in CT images, comprises the following steps:

- providing a CT scan dataset comprising CT scan data of the same object at at least two different energies,
- calculating a plurality of spatially resolved first material density values for a first substance type from the CT scan data of the CT scan dataset,
- calculating a plurality of correction factors based on the calculated first material density values, wherein each correction factor is assigned to a second material density value for a second substance type,
- calculating CT images from the material density values, wherein at least one of the CT images is corrected using the correction factors.

In particular, the method is used to correct material-induced effects such as mass and/or volume effects in virtual non-calcium images (VNCa images) or virtual non-contrast images (VNC images) as CT images. Basically, the second material density values or CT images created therefrom should be corrected as part of the correction.

In particular, the method can be a computer-implemented method.

For the purposes of example embodiments of the present invention, the term "CT scan data" means raw CT data but also data from reconstructed CT images. The CT scan data preferably has the same format at different energies, i.e. either raw CT data or reconstructed CT images are used for all energies. The term "CT scan dataset" refers to the entirety of the CT images used (at all energies). Thus, a CT scan dataset comprises at least two sets of CT scan data acquired at different energies, or different energy ranges, or different (X-ray) energy spectra. These are in particular dual-energy CT data or photon-counting CT data. If the method is performed using reconstructed images, the CT scan data consists of pixels or voxels of the reconstructed images (with the corresponding CT values, e.g. in HU). Proceeding from raw data (e.g. sinograms), the CT scan data consists of raw data values from which images can be reconstructed.

For a good understanding of example embodiments of the present invention, the CT scan data can be conceived of as being made up of a plurality of CT values c. This CT data c, just like the material density values d, material values m and correction factors r, indicates the state in a partial volume. A partial volume is represented in a (reconstructed) CT image as a voxel or as a pixel. The aforementioned quantities thus indicate the state in a partial volume at a particular position and would therefore have to be specified more precisely as c (x,y,z), d (x,y,z), m (x,y,z) and r (x,y,z). In calculations, the quantities used there always refer to the same partial volume. Thus, a material density value d (x0,y0,z0) is always calculated from CT values c (x0,y0,z0) for the same partial volume and corrections of a material density value m (x0,y0,z0) are performed using correction factors r (x0,y0,z0) for the same partial volume. In the following, these coordinates will be omitted for the sake of clarity. However, it should always be borne in mind that the calculations in question are carried out for a large number of values at different (image) positions and that the values of the same positions (same partial volumes) are always used. If a plurality of values are calculated, this means that the corresponding values are calculated for a plurality of partial volumes so that the partial volumes result in a coherent volume, namely a CT image of the object.

A CT scan dataset can be provided simply by taking a CT scan or by downloading a corresponding dataset via a data network, e.g. as part of a radiological information system (RIS) or a picture archiving and communication system (PACS).

The CT scan data must show the same object, e.g. a body region, at different energies. Corresponding acquisition methods are well known from the prior art.

Calculating a plurality of material density values d is widely known from the prior art. For example, this is often based on a CT value c1 from a scan at a first energy and a second CT value c2 from a scan at a second energy by solving the system of equations $$c1=a1,1\cdot d1+a1,2\cdot d2+a1,3\cdot(1-d2) \quad (1)$$

$$c2=a2,1\cdot d1+a2,2\cdot d2+a2,3\cdot(1-d2).$$

The material density values d indicate local material densities (in a partial volume at position x,y,z in each case) relative to reference densities. These values are well known from the prior art.

The coefficients ai,k reflect the enhancement of the CT value (also known as density enhancement) due to the presence of material k (1, 2 or 3) with a concentration β (or better βk,ref) in the spectrum at an energy i (1 or 2) and apply to all coordinates. Therefore, the same ai,k preferably always apply to all ci (x,y,z) and dk (x,y,z). These coefficients are often determined (e.g. for iodine or calcium) by calibration measurements and are typically used to calculate VNC, VNCa or other material maps showing the enhancement of the CT value by a base material at a reference energy. If the coefficients ai,3=0, as is advantageous when only two materials, e.g. iodine and water, are to be separated, this system of equations can also be represented in vector notation using the matrix A (containing the coefficients ai,k where i=1 or 2 and k=1 or 2) as follows:

$$A\begin{pmatrix} d_1 \\ d_2 \end{pmatrix} = \begin{pmatrix} c_1 \\ c_2 \end{pmatrix}. \quad (2)$$

As noted above, these equations relate to only one partial volume (e.g. voxel) in each case and that the calculation is performed for each (relevant) partial volume in the image volume.

Usually, both material density values (the first and the second) are calculated. To carry out the method, however, only a first material density value is initially required. However, the second material density value can obviously also be calculated. In practice, it is advantageous if the first material density value relates to the substance type iodine, calcium or hydroxylapatite as the first substance type. The term "substance type" denotes a material or substance, or a mixture of materials. Basically, it can be assumed that this means a type of substance or mixture of substances of a body region which may well have a very complex structure.

Thus, proceeding from two CT scans showing the same body region acquired at different energies with the different CT values ci, the material density values dk (x,y,z) (with k=1,2 or k=1,2,3) for each voxel at position (x,y,z) are calculated from the corresponding ci(x,y,z) (with i=1,2).

The large number of correction factors that are then calculated are also calculated for the respective partial volumes. They are basically used to create a (second) material map, e.g. a VNC image or a VNCa image. Thus, a correction factor r(x,y,z) is calculated in each case from the first material density value d1(x,y,z) for a partial volume at position (x,y,z). Each correction factor is thus also assigned to a second material density value d2(x,y,z) for that partial volume, at least if such a value is available. Since, as shown above, the two material density values can be calculated for each position by solving the equations, this presents no problem. The second substance type should be iodine-free body substance (if the first substance type is iodine) or red and white bone marrow (if the first substance type is calcium or hydroxylapatite). However, calcium-water decomposition may well take place if the first substance type is calcium (or HA) and the second substance type is water. Water can also be considered representative of all substance types that are approximately spectrally neutral, i.e. $c1\approx c2$. A change in chemical composition, e.g. from fat to muscle tissue, would then appear in the corresponding CT image (in particular a VNCa image) as a change in density of the water content. The method according to embodiments of the present invention can then correct for the effect of volume displacement by the first substance type (e.g. calcium).

The CT images that are calculated as a result are preferably material maps, e.g. a CT image showing calcium and a (corrected) VNCa image. Theoretically, however, other CT images are also possible. For the correction, a CT image can be calculated first and then corrected, but it is also possible to correct the second material density values (at all image positions) and create a CT image from the corrected second material density values.

An advantage of the method according to embodiments of the present invention is that a 2- or 3-material decomposition can initially be calculated based only on the measured CT values without taking volume effects into account. This allows corrections to be made based directly on the actual measured values in each case without the use of estimates or models. It is quite possible to then correct for volume effects empirically. The advantage is that only the specific density of a base material (e.g. calcium) needs to be known and not the density of complex, endogenous materials (or "substance types"), which is often neither really known nor readily measurable.

An apparatus according to an embodiment of the present invention for correcting material-induced effects in CT images is particularly designed for carrying out a method according to an embodiment of the present invention. The apparatus comprises the following components:

a data interface designed to receive a CT scan dataset comprising CT scan data of the same object at at least two different energies, a density value unit designed to calculate a plurality of spatially resolved first material density values for a first substance type from the CT scan data of the CT scan dataset, a correction factor unit designed to calculate a plurality of correction factors based on the calculated first material density values, wherein each correction factor is assigned to a second material density value for a second substance type, an imaging unit designed to calculate CT images from the material density values, wherein at least one of the CT images is corrected via the correction factors.

The mode of operation of these components has already been described above.

A diagnostic facility according to an embodiment of the present invention is used by a person for diagnostic purposes and can be constituted e.g. by a computer system with a screen, the system being designed to calculate and display CT images. Such diagnostic facilities are basically known from the prior art. The difference compared to the prior art is that the diagnostic facility comprises an apparatus according to an embodiment of the present invention. Alternatively or additionally, the diagnostic facility is designed to carry out a method according to an embodiment of the present invention.

A control facility according to an embodiment of the present invention is designed to control a CT system. Such control facilities are basically known from the prior art. The difference compared to the prior art is that the control facility comprises an apparatus according to an embodiment of the present invention. Alternatively or additionally, the control facility is designed to carry out a method according to an embodiment of the present invention.

A CT system according to an embodiment of the present invention comprises a dual-energy CT scanner, a multi-energy CT scanner or a photon-counting CT scanner and a control facility according to an embodiment of the present invention.

In particular, embodiments of the present invention can be implemented in the form of a computer unit, in particular in a control facility for a CT system or in a diagnostic facility, using suitable software. For this purpose, the computer unit can, for example, have one or more cooperating microprocessors or the like. In particular, embodiments of the present invention can be implemented in the form of suitable software program sections in the computer unit. The advantage of a largely software-based implementation is that currently used computer units in CT systems or diagnostic facilities can also be upgraded in a simple manner via a software or firmware update in order to operate in the manner according to embodiments of the present invention. In this respect, the object is also achieved by a corresponding computer program product comprising a computer program that can be loaded directly into a memory device of a computer unit, having program sections for carrying out all the steps of the method according to embodiments of the present invention when the program is executed in the computer unit. As well as the computer program, such a computer program product can optionally comprise additional elements, such as a documentation and/or additional components, including hardware components, such as hardware keys (dongles, etc.) for using the software. A computer-readable medium, e.g. a memory stick, hard disk or other portable or permanently installed data carrier on which the program sections of the computer program that can be read in and executed by a computer unit are stored, can be used for transfer to the computer unit and/or for storage on or in the computer unit.

Other particularly advantageous embodiments and developments of embodiments will emerge from the dependent claims and the following description, wherein the claims of one claim category can also be further developed analogously to the claims and sections of the description relating to another claim category and, in particular, individual features of different exemplary embodiments or variants can also be combined to form new exemplary embodiments or variants.

In particular, the features and advantages described in connection with the method according to embodiments of the present invention can also be developed as corresponding subunits of the apparatus according to embodiments of the present invention. Conversely, the features and advantages described in connection with the apparatus according to embodiments of the present invention can also be developed as corresponding process steps of the method according to embodiments of the present invention.

According to a preferred method, the CT scan data comprises CT values (c; i.e. the CT scan data is constituted by CT values c), wherein a plurality of first CT values (c1) have been acquired at a first energy and a plurality of second CT values (c2) have been acquired at a second energy. This is prior art practice for dual-energy CT (DECT) but also for photon-counting CT (PCCT). A plurality of first material density values d1 and second material density values d2 are then calculated from the CT values (c1, c2), wherein each pair d1, d2 of material density values indicates the situation in an individual partial volume (voxel). These material density values are calculated from CT values relating to corresponding partial volumes (voxels). Thus, material density values dk (x,y,z) are calculated from CT values ci (x,y,z) for a partial volume and the plurality of calculated values reflects the acquired volume.

The material density values for a partial volume having a first CT value c1 and a second CT value c2 are calculated by solving the system of equations $$c1=a1,1\cdot d1+a1,2\cdot d2+a1,3\cdot(1-d2) \text{ (see equation 1 above)}$$

$$c2=a2,1\cdot d1+a2,2\cdot d2+a2,3\cdot(1-d2)$$

using predetermined coefficients ai,k, wherein ai,3≠0 if the second substance type contains a mixture of two or more substances (e.g. red and white bone marrow) and ai,3=0 if the second substance type is assumed to be only a single substance.

According to a preferred method, a material map is calculated as a CT image. A first material map is calculated from a plurality of first material density values and/or a second material map is calculated from a plurality of second material density values. The second material map and its correction will be discussed in more detail below.

Material values m1 (actually m1 (x,y,z)) of the first material map are preferably calculated using a predetermined weighting factor w according to the following formula:

$$m1=d1\cdot(w\cdot a1,1+(1-w)\cdot a2,1). \quad (3)$$

The weighting factor w is preferably in an interval between 0 and 1 and, with particular preference, is not location-dependent. The same weighting factor w preferably applies to all partial volumes (i.e. to all m1 (x,y,z)).

According to a preferred method, a correction factor r is calculated from a function $$r=(1-b\cdot d1)-1. \quad (4)$$

In this way, a plurality of correction factors r (x,y,z) are calculated for a large number of partial volumes (for a large number of partial volumes/voxels of the acquired volume), wherein b is a constant factor over the plurality of correction factors (i.e. is the same for all partial volumes or all r (x,y,z)). It is preferred that $$b=\beta/\rho \quad (5)$$

with a specific density ρ of the first substance type (e.g. for calcium 3.16 g/sq cm) and a predetermined mass density β of the first substance type. The mass density β is preferably selected such that the associated enhancement in the CT values is in clinically useful ranges.

The mass density β (or provided with a subscript k for the respective material and an indication of its function as a reference βk,ref) is the same for all correction factors (thus for the first substance type, a β1,ref is used for all r). Since the coefficients ai,k describe the enhancement of the CT value, a local density d1β1,ref can be estimated from the CT measurements. In practice, the coefficients ai,k (and therefore also β1,ref) are determined by measuring phantoms having known material densities at both energies.

According to a preferred method, coefficients ai,k for calculating a material map and/or for calculating material density values are determined by calibration measurements for the predetermined mass density β of the first substance type. As indicated above, a phantom having known concentrations or material densities can be scanned at both energies for the calibration measurements. The CT values in the inserts, i.e. the cylindrical inserts of the phantom with known material concentrations, are then measured on the reconstructed images.

According to a preferred method, a CT image is corrected via a monotonic correction function f of the correction factor (r), preferably a correction factor r as described above. This monotonic correction function is preferably multiplied by corresponding image values of an uncorrected CT image or, when creating a CT image, is multiplied by a second material density value used for the creation thereof. Thus, if one of the CT images is a second material map with the material values m2, the second material map is preferably corrected with m2·f(r), or a value d2 for calculating a CT image (e.g. the second material map) is preferably corrected with d2·f(r).

According to a preferred method, the monotonic function f is the identity or a root function of the correction factor, e.g. $f(r)=r$ or $f(r)=\sqrt{r}$. Alternatively or additionally, in the case where the correction factor exceeds a limit value G, the correction factor is damped or limited. This can be done e.g. for the function f(r)=r by selecting f(r)=f(r) for r<G and f(r)=f(G) for r>G. The root function is advantageous because it can damp very strong corrections. Practice shows that theoretically correct calculations can also result in overcorrections or even artifacts in extreme cases. The limit value has the advantage that the correction can thus be limited to a physically reasonable maximum.

According to a preferred method, a second material map is calculated as a CT image from a plurality of second material density values. It is preferable for material values m2 of the second material map to be calculated via a correction function f (for different partial volumes) and a predetermined weighting factor w. The same applies to this weighting factor w as was explained above for the first material map, wherein in particular the same weighting factor w is selected for both material maps. The material values m2 are preferably calculated according to the formula $$m2=d2\cdot(w\cdot(a1,2-a1,3)+(1-w)\cdot(a2,2-a2,3))\cdot f \quad (6)$$

where i=1 or 2, a1,3≠0 and a2,3≠0 if the second substance type contains a mixture of two or more substances (e.g. red and white bone marrow) and a1,3=0 and a2,3=0 if the second substance type is assumed to be only a single substance.

The following are therefore preferably calculated using the correction factor r $$m2=d2\cdot(w\cdot(a1,2-a1,3)+(1-w)\cdot(a2,2-a2,3))\cdot r \text{ or}$$

$$m2=d2\cdot(w\cdot(a1,2-a1,3)+(1-w)\cdot(a2,2-a2,3))\sqrt{r} \text{ or}$$

$$m2=d2\cdot(w\cdot(a1,2-a1,3)+(1-w)\cdot(a2,2-a2,3))\cdot f(r) \text{ for } r<G \text{ and}$$

$$m2=d2\cdot(w\cdot(a1,2-a1,3)+(1-w)\cdot(a2,2-a2,3))\cdot f(G) \text{ for } r>G.$$

According to a preferred method, the first substance type is iodine or iodine-containing body substance or calcium or calcium-containing body substance, in particular hydroxylapatite. In the case where the first substance type comprises iodine, the second substance type is preferably water and/or iodine-free body substance. In the case where the first substance type comprises calcium, the second substance type is water or comprises yellow and red bone marrow.

To calculate the material density values, the material maps and not least the correction factors, AI-based methods (AI: "artificial intelligence") are preferably used for the method according to embodiments of the present invention. Artificial intelligence is based on the principle of machine learning and is generally implemented using an adaptive algorithm that has been trained accordingly. The term "machine learning" as used here also includes the principle of "deep learning".

Components of embodiments of the present invention are preferably present as a "cloud service". A cloud service of this kind is used to process data, in particular via artificial intelligence, but can also be a service based on conventional algorithms or a service in which evaluation by humans takes place in the background. In general, a cloud service (hereinafter also referred to as a "cloud" for short) is an IT infrastructure in which e.g. storage space or computing power and/or application software is provided via a network. Communication between the user and the cloud takes place via data interfaces and/or data transfer protocols. In the present case, it is particularly preferred that the cloud service provides both computing power and application software.

In the context of a preferred method, a CT scan dataset is provided via the network to the cloud service. This comprises a computing system, e.g. a computer cluster, which can execute the method according to embodiments of the present invention and which generally does not include the user's local computer. In particular, this cloud can be provided by the medical facility that also provides the medical technology systems. For example, the data of an image acquisition is sent to a (remote) computer system (the cloud) via a RIS (radiological information system) or PACS. The computing system of the cloud, the network, and the medical system preferably represent an interconnection in data technology terms. The method can be implemented via a command constellation in the network. The data calculated in the cloud ("result data") is subsequently sent back to the user's local computer via the network.

BRIEF DESCRIPTION OF THE DRAWINGS

The present invention will now be explained in more detail on the basis of exemplary embodiments and with reference to the accompanying figures. In the various figures, identical components are provided with the same reference numerals in each case. The figures are generally not to scale.

DETAILED DESCRIPTION

Figure 1:
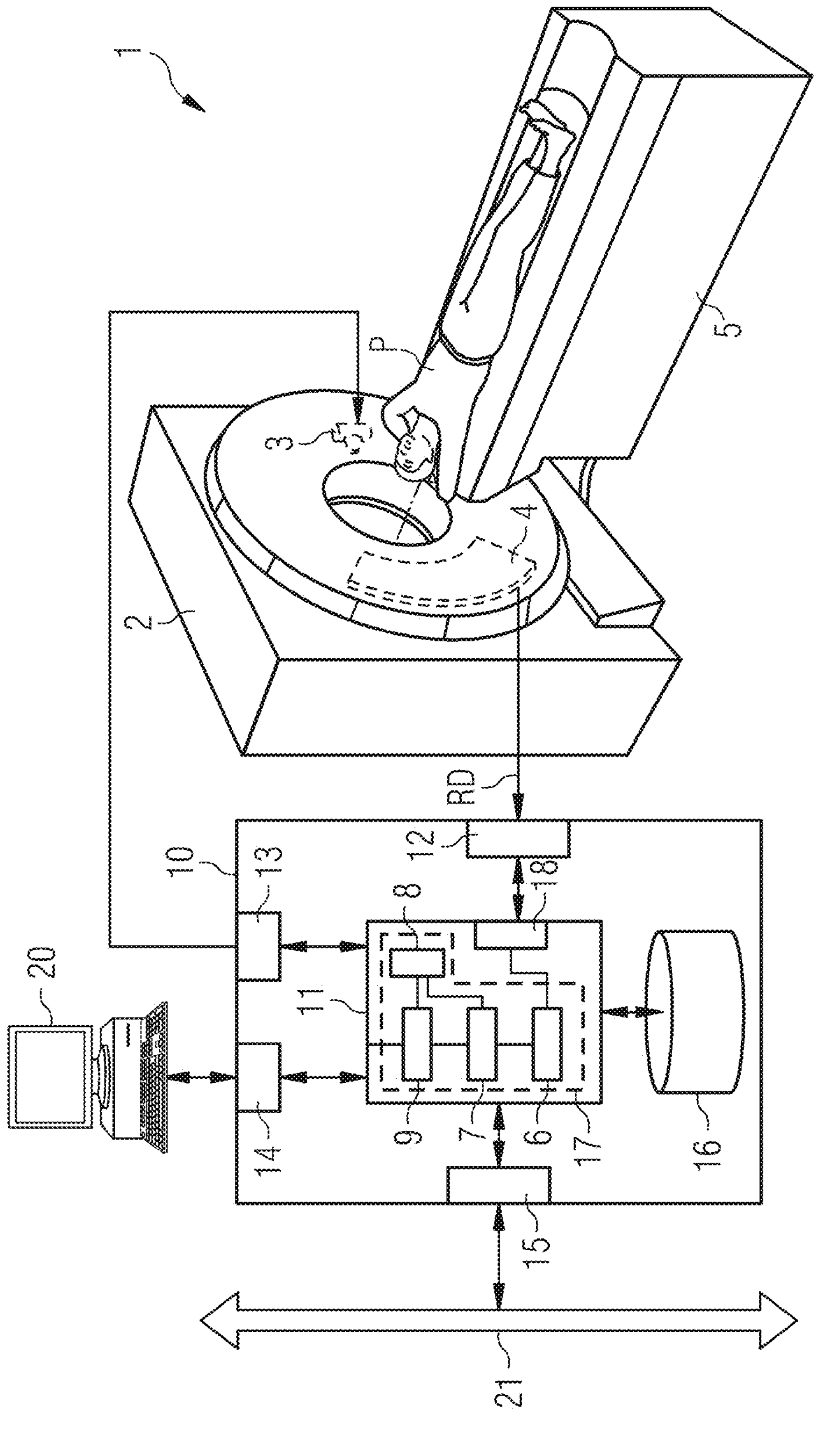
FIG. 1 shows the typical setup of a CT system having a system according to an embodiment of the present invention.

FIG. 1 shows a rough schematic of a computed tomography system 1 having a control facility 10 for carrying out the method according to an embodiment of the present invention. The computed tomography system 1 has, in the usual manner, a scanner 2 having a gantry in which an X-ray source 3 rotates and irradiates a patient P who is moved into a measuring chamber of the gantry on a couch 5 so that the radiation is incident on a detector 4 located opposite the X-ray source 3. The scanner 2 is designed for dual/multi energy CT or photon-counting CT imaging. It is expressly understood that the exemplary embodiment as shown in this figure is merely an example of CT and the present invention can also be used on any CT designs, e.g. with annular fixed X-ray detector and/or a plurality of X-ray sources.

Likewise, in the case of the control facility 10, only the components that are essential for explaining embodiments of the present invention are shown. Basically, such CT systems and associated control facilities are familiar to persons skilled in the art and do not therefore need to be explained in detail.

A core component of the control facility 10 is here a processor 11 on which various components are implemented in the form of software modules. The control facility 10 also has a terminal interface 14 to which a terminal 20 is connected via which an operator can operate the control facility 10 and thus the computed tomography system 1. This terminal 20 can also be used as a diagnostic facility 20.

Another interface 15 is a network interface for connection to a data bus 21 in order to establish a connection to a RIS (radiological information system) or PACS (picture archiving and communication system).

The scanner 2 can be controlled by the control facility 10 via a control interface 13, i.e. the rotation speed of the gantry, the movement of the patient couch 5 and the X-ray source 3 itself, for example, are controlled.

The raw data RD is read from the detector 4 via an acquisition interface 12. In addition, the control facility 10 has a memory unit 16 in which, among other things, various measurement logs are stored.

A component on the processor 11 is an image data reconstruction unit 18 which is used to reconstruct the desired image data from the raw data RD obtained via the data acquisition interface 12. In this example, it is assumed that this image data reconstruction unit 18 provides the CT values c1, c2.

Figure 4:
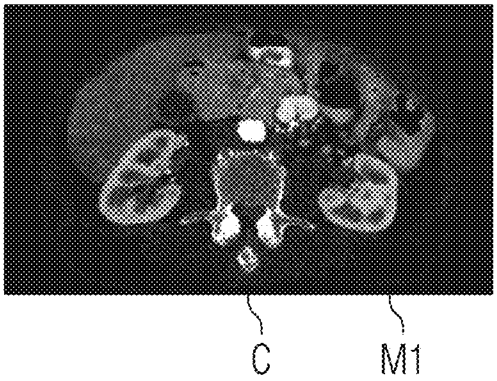
FIG. 4 shows an example of a possible CT image in the form of an iodine map.

An apparatus 17 for correcting material-induced effects in CT images C is implemented in the processor 11. The apparatus 17 comprises the following components, which are preferably implemented as software units. For example, the apparatus is designed here to carry out a method as shown in FIG. 4.

A data interface 6 designed to receive a CT scan dataset A. This CT scan dataset A comprises CT scan data A1, A2 of the same object at at least two different energies. This data interface here receives the reconstructed image data of the image data reconstruction unit 18.

A density value unit 7 designed to calculate a plurality of spatially resolved first material density values D1 for a first substance type from the CT scan data A1, A2 of the CT scan dataset A.

A correction factor unit 8 designed to calculate a plurality of correction factors K based on the calculated first material density values D1, wherein each correction factor K is assigned to a second material density value D2 for a second substance type S2.

An imaging unit 9 designed to calculate CT images C from the material density values D1, D2, wherein at least one of the CT images C is corrected via the correction factors K.

In the case where the terminal 20 is used as a diagnostic facility 20, the entire apparatus 17 can alternatively or once again be implemented in said terminal 20.

Figure 2:
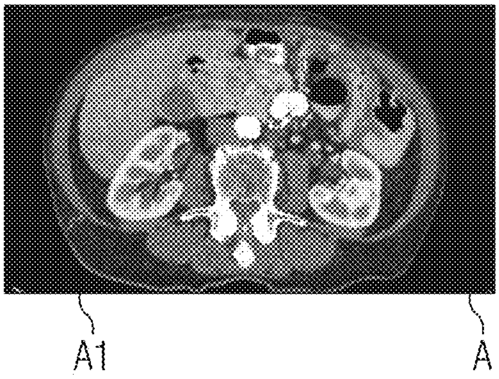
FIG. 2 shows an example of possible CT scan data at low energy.
Figure 3:
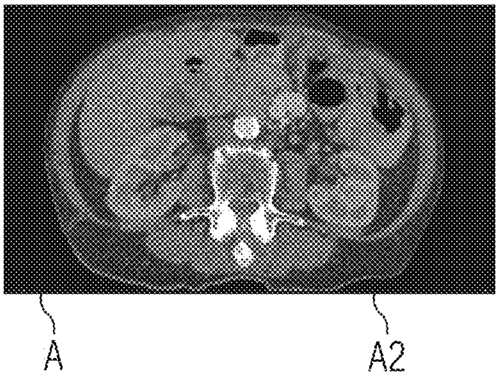
FIG. 3 shows an example of possible CT scan data at high energy.

FIGS. 2, 3 show examples of possible CT scan data A1, A2, which here constitute a scan dataset A. FIG. 2 shows CT scan data A1 for a lower energy of the X-ray radiation and FIG. 3 shows CT scan data A1 for a higher energy of the X-ray radiation.

Figure 5:
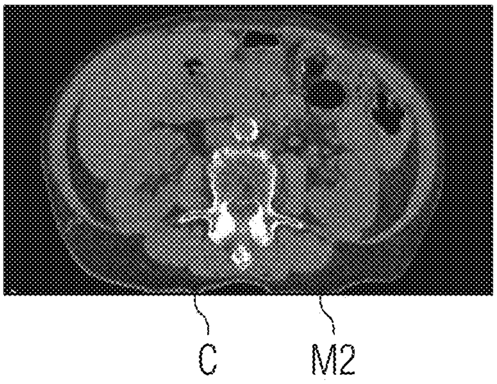
FIG. 5 shows an example of a possible CT image in the form of a VNC image.

FIGS. 4 and 5 show examples of possible CT images C. FIG. 4 (left) shows a typical CT image in the form of an iodine map M1 as an example of a first material map M1. FIG. 5 on the right shows a VNC image M2 as an example of a second material map M2. In FIG. 4 it can be seen that the iodine-containing structures of FIGS. 2 and 3 are clearly visible, but hardly any other structures, and in FIG. 5 the remaining structures of FIGS. 2 and 3.

Figure 6:
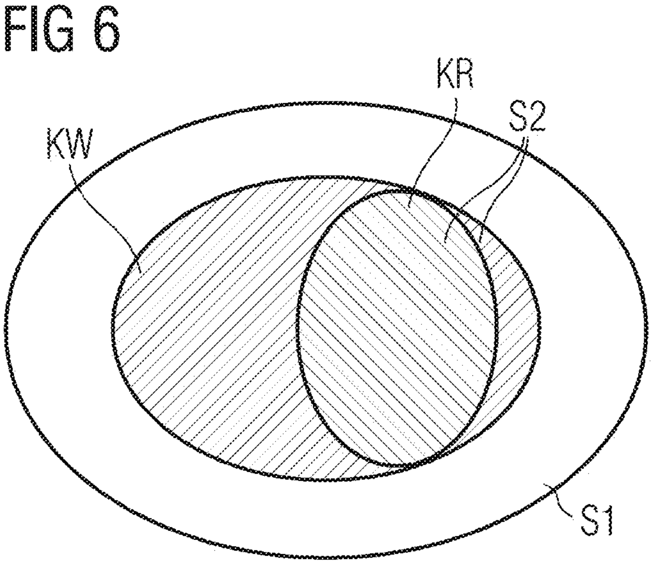
FIG. 6 shows a diagram of a bone with a calcium structure and white and red bone marrow.

FIG. 6 shows a diagram of a bone with a calcium structure as the first substance type S1 and white bone marrow K1 and red bone marrow K2 as the second substance type S2. If this bone had been photographed as FIGS. 2 and 3, the calcium as the first substance type S1 could be shown in a calcium image and the second substance type S2 could be shown in a VNCa image similarly to the iodine image of FIG. 4 and the VNC image of FIG. 5, wherein white bone marrow K1 and red bone marrow K2 could be separated using different shades of gray reflecting the HU.

Figure 7:
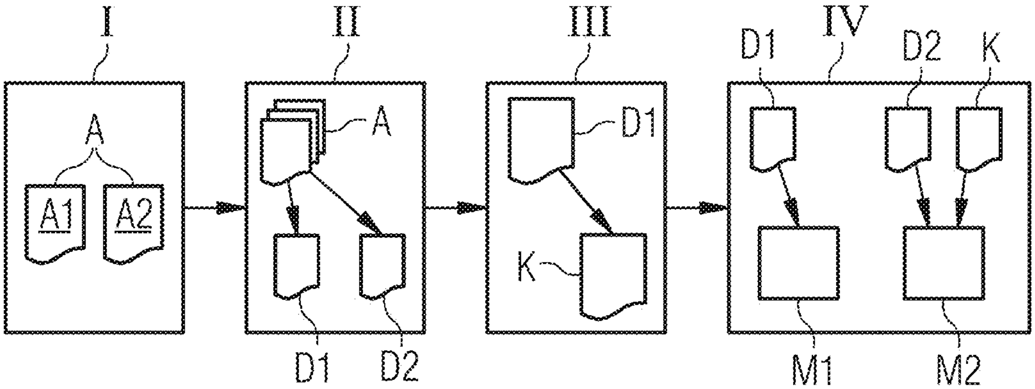
FIG. 7 shows a block diagram of an exemplary embodiment of a method according to the present invention.

FIG. 7 shows a block diagram of an exemplary embodiment of a method according to the present invention for correcting material-induced effects in CT images C.

In step I, a CT scan dataset A comprising CT scan data A1, A2 of the same object at at least two different energies is provided. Here this CT scan dataset A is available, for example, after reconstruction by an image data reconstruction unit 18 according to FIG. 1 as reconstructed image data with CT values c1, c2. This could be envisioned as shown in FIGS. 2 and 3.

In step II, a plurality of spatially resolved first material density values D1 (d1) for a first substance type S1 are calculated from the CT scan data A1, A2 of the CT scan dataset A. This can be done, for example, by solving the system of equations $$c1=a1,1\cdot d1+a1,2\cdot d2+a1,3\cdot 1-d2$$

$$c2=a2,1\cdot d1+a2,2\cdot d2+a2,3\cdot 1-d2$$

with predefined coefficients ai,k which are the same for all material density values D1, D2. These coefficients ai,k can be determined from calibration measurements based on a predetermined mass density β (which is the same for all partial volumes). The ai,1 represent calcium, the ai,2 white bone marrow K1, and the ai,3 red bone marrow K2 (see e.g. FIG. 6).

In step III, a plurality of correction factors K are calculated based on the calculated first material density values D1. Each correction factor K is assigned to a second material density value D2 for a second substance type S2. Considering FIG. 5, each pixel of this figure would be assigned an individual second material density value D2 and therefore also an individual correction factor K. A correction factor K (r) can be calculated from a function $$r=(1-\beta/\rho\cdot d1)-1$$

using the specific density ρ of the first substance type S1 (e.g. 3.16 g/sq cm for calcium) and a predetermined mass density β of the first substance type S1.

In step IV, material maps M1, M2 are calculated as CT images C from the material density values D1, D2, wherein the second material map M2 is created from the second material density values D2 and corrected via the correction factors. A material map M1, M2 is then calculated using the material values m1 for the first material map M1 and the material values m2 for the second material map M2, e.g. according to the formulas $$m1=d1\cdot(w\cdot a1,1+(1-w)\cdot a1,2) \text{ and}$$

$$m2=d2\cdot(w\cdot(a1,2-a1,3)+(1-w)\cdot(a2,2-a2,3))\cdot r.$$

Finally, it is reiterated that the methods described in detail above and the computed tomography system 1 depicted are merely exemplary embodiments which can be modified by persons skilled in the art in a wide variety of ways without departing from the scope of the present invention. In addition, the use of the indefinite articles “a” or “an” does not exclude the possibility that the features in question may be present more than once. Similarly, the terms “unit” and “module” do not preclude the components in question from comprising a plurality of interacting sub-components which may possibly also be spatially distributed.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments. As used herein, the term “and/or,” includes any and all combinations of one or more of the associated listed items. The phrase “at least one of” has the same meaning as “and/or”.

Spatially relative terms, such as “beneath,” “below,” “lower,” “under,” “above,” “upper,” and the like, may be used herein for ease of description to describe one element or feature’s relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as “below,” “beneath,” or “under,” other elements or features would then be oriented “above” the other elements or features. Thus, the example terms “below” and “under” may encompass both an orientation of above and below. The device may be otherwise oriented (rotated 90 degrees or at other orientations) and the spatially relative descriptors used herein interpreted accordingly. In addition, when an element is referred to as being “between” two elements, the element may be the only element between the two elements, or one or more other intervening elements may be present.

Spatial and functional relationships between elements (for example, between modules) are described using various terms, including “on,” “connected,” “engaged,” “interfaced,” and “coupled.” Unless explicitly described as being “direct,” when a relationship between first and second elements is described in the disclosure, that relationship encompasses a direct relationship where no other intervening elements are present between the first and second elements, and also an indirect relationship where one or more intervening elements are present (either spatially or functionally) between the first and second elements. In contrast, when an element is referred to as being “directly” on, connected, engaged, interfaced, or coupled to another element, there are no intervening elements present. Other words used to describe the relationship between elements should be interpreted in a like fashion (e.g., “between,” versus “directly between,” “adjacent,” versus “directly adjacent,” etc.).

The terminology used herein is for the purpose of describing particular embodiments only and is not intended to be limiting of example embodiments. As used herein, the singular forms “a,” “an,” and “the,” are intended to include the plural forms as well, unless the context clearly indicates otherwise. As used herein, the terms “and/or” and “at least one of” include any and all combinations of one or more of the associated listed items. It will be further understood that the terms “comprises,” “comprising,” “includes,” and/or “including,” when used herein, specify the presence of stated features, integers, steps, operations, elements, and/or components, but do not preclude the presence or addition of one or more other features, integers, steps, operations, elements, components, and/or groups thereof. As used herein, the term “and/or” includes any and all combinations of one or more of the associated listed items. Expressions such as “at least one of,” when preceding a list of elements, modify the entire list of elements and do not modify the individual elements of the list. Also, the term “example” is intended to refer to an example or illustration.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

It is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed above. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments. The present invention may, however, be embodied in many alternate forms and should not be construed as limited to only the embodiments set forth herein.

In addition, or alternative, to that discussed above, units and/or devices according to one or more example embodiments may be implemented using hardware, software, and/or a combination thereof. For example, hardware devices may be implemented using processing circuitry such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

In this application, including the definitions below, the term 'module' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion.

In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without sub-dividing the operations and/or functions of the computer processing units into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor; however, one skilled in the art will appreciate that a hardware device may include multiple processing elements or processors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one example embodiment relates to the non-transitory computer-readable storage medium including electronically readable control information (processor executable instructions) stored thereon, configured in such that when the storage medium is used in a controller of a device, at least one embodiment of the method may be carried out.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

Although the present invention has been shown and described with respect to certain example embodiments, equivalents and modifications will occur to others skilled in the art upon the reading and understanding of the specification. The present invention includes all such equivalents and modifications and is limited only by the scope of the appended claims.

What is claimed is:

1. A computer-implemented method for correcting material-induced effects in CT images, the computer-implemented method executed by an apparatus for correcting material-induced effects in CT images, the apparatus including at least one processor and a memory, the memory storing computer-executable instructions that, when executed by the at least one processor, cause the at least one processor to perform the computer-implemented method, wherein the computer-implemented method comprises:

providing a CT scan dataset including CT scan data of an object at at least two different energies;

calculating a plurality of first material density values for a first substance type based on the CT scan data of the CT scan dataset, the plurality of first material density values being spatially resolved material density values;

calculating a plurality of correction factors based on the plurality of first material density values, wherein each correction factor is assigned to a second material density value, among a plurality of second material density values, for a second substance type;

calculating CT images based on the plurality of first material density values and the plurality of second material density values, wherein at least one of the CT images is corrected via the plurality of correction factors; and at least one of outputting or displaying the CT images corrected via the plurality of correction factors.

2. The computer-implemented method as claimed in claim 1, wherein the CT scan data includes CT values, wherein a plurality of first CT values have been acquired at a first energy and a plurality of second CT values have been acquired at a second energy, and the plurality of first material density values $d_1$ and the plurality of second material density values $d_2$ are calculated based on the plurality of first CT values and the plurality of second CT values, wherein each pair of said plurality of first material density values and said plurality of second material density values indicates a situation in an individual partial volume and said plurality of first material density values and said plurality of second material density values are calculated based on CT values relating to a corresponding partial volume, and wherein material density values for a partial volume having a first CT value $c_1$ and a second CT value $c_2$ are calculated by solving a system of equations including $$c_1 = a_{1,1} \cdot d_1 + a_{1,2} \cdot d_2 + a_{1,3} \cdot (1 - d_2)$$

$$c_2 = a_{2,1} \cdot d_1 + a_{2,2} \cdot d_2 + a_{2,3} \cdot (1 - d_2)$$

using coefficients $a_{i,k}$ wherein $a_{i,3} \neq 0$ when the second substance type contains a mixture of two or more substances and $a_{i,3}=0$ when the second substance type is assumed to be only a single substance.

3. The computer-implemented method as claimed in claim 2, wherein a first material map is calculated from the plurality of first material density values as a CT image, and wherein material values $m_1$ of the first material map are calculated via a weighting factor w according to the formula $m_1=d_1(w \cdot a_{1,1}+(1-w) \cdot a_{1,2})$.

4. The computer-implemented method as claimed in claim 2, wherein a correction factor r is calculated according to a function $$r = (1 - b \cdot d_1)^{-1},$$

wherein b is a constant factor over the plurality of correction factors, and wherein $b=\beta/\rho$, with a density $\rho$ of the first substance type and a mass density $\beta$ of the first substance type.

5. The computer-implemented method as claimed in claim 4, wherein the coefficients $a_{i,k}$ for at least one of calculating a material map or calculating material density values are determined by calibration measurements for the mass density $\beta$ of the first substance type.

6. The computer implemented method as claimed in claim 4, wherein a CT image is corrected via a monotonic correction function f of the correction factor r, wherein the monotonic correction function f is multiplied by corresponding image values of an uncorrected CT image or, for creating a CT image, is multiplied by a second material density value used for creating the CT image.

7. The computer implemented method as claimed in claim 6, wherein at least one of the monotonic correction function f is an identity or a root function of the correction factor r, or in case the correction factor r exceeds a limit value G, the correction factor r is damped or limited, and for the correction factor r, the following apply to the monotonic correction function f(r)

$f(r)=r$, $f(r)=\sqrt{r}$, and $f(r)=f(r)$ for $r<G$ and $f(r)=f(G)$ for $r>G$.

8. The computer-implemented method as claimed in claim 7, wherein a second material map is calculated from the plurality of second material density values as a CT image, wherein material values of the second material map are calculated via a weighting factor w and the monotonic correction function f according to the formula $$m_2 = d_2 \cdot (w \cdot (a_{1,2} - a_{1,3}) + (1 - w) \cdot (a_{2,2} - a_{2,3})) \cdot f,$$

where i=1 or 2, $a_{1,3} \neq 0$ and $a_{2,3} \neq 0$ when the second substance type contains a mixture of two or more substances and $a_{1,3} \neq 0$ and $a_{2,3} \neq 0$ when the second substance type is assumed to be only a single substance.

9. The computer-implemented method as claimed in claim 6, wherein a second material map is calculated from the plurality of second material density values as a CT image, wherein material values of the second material map are calculated via a weighting factor w and the monotonic correction function f according to the formula $$m_2 = d_2 \cdot (w \cdot (a_{1,2} - a_{1,3}) + (1 - w) \cdot (a_{2,2} - a_{2,3})) \cdot f,$$

where i=1 or 2, $a_{1,3} \neq 0$ and $a_{2,3} \neq 0$ when the second substance type contains a mixture of two or more substances and $a_{1,3} \neq 0$ and $a_{2,3} \neq 0$ when the second substance type is assumed to be only a single substance.

10. The computer-implemented method as claimed in claim 2, wherein a first material map is calculated from the plurality of first material density values as a CT image.

11. The computer-implemented method as claimed in claim 1, wherein the first substance type is iodine or an iodine-containing body substance or calcium or a calcium-containing body substance.

12. The computer implemented method as claimed in claim 11, wherein the first substance type is hydroxylapatite.

13. The computer-implemented method as claimed in claim 11, wherein the first substance type includes iodine and the second substance type is water or an iodine-free body substance, or the first substance type includes calcium and the second substance type is water or includes yellow and red bone marrow.

14. A non-transitory computer program product comprising computer-executable instructions that, when executed by a computer, cause the computer to carry out the computer-implemented method as claimed in claim 1.

15. A non-transitory computer-readable storage medium comprising computer-executable instructions that, when executed by a computer, cause the computer to carry out the computer-implemented method as claimed in claim 1.

16. The computer implemented method as claimed in claim 1, wherein the CT scan data includes CT values, wherein a plurality of first CT values have been acquired at a first energy and a plurality of second CT values have been acquired at a second energy, and the plurality of first material density values and the plurality of second material density values are calculated based on the plurality of first CT values and the plurality of second CT values, wherein each pair of said plurality of first material density values and said plurality of second material density values indicates a situation in an individual partial volume and said plurality of first material density values and said plurality of second material density values are calculated based on CT values relating to a corresponding partial volume.

17. The computer-implemented method as claimed in claim 1, wherein a CT image is corrected via a monotonic correction function of a correction factor.

18. The computer-implemented method as claimed in claim 17, wherein the first substance type is iodine or an iodine-containing body substance or calcium or a calcium-containing body substance.

19. A diagnostic facility configured to assess CT images, said diagnostic facility comprising an apparatus configured to perform the computer-implemented method of claim 1.

20. A control facility for a CT system, said control facility comprising an apparatus configured to perform the computer-implemented method of claim 1.

21. An apparatus for correcting material-induced effects in CT images, the apparatus comprising:

a data interface configured to receive a CT scan dataset including CT scan data of an object at at least two different energies;

a density value unit configured to calculate a plurality of first material density values for a first substance type based on the CT scan data of the CT scan dataset, the plurality of first material density values being spatially resolved material density values;

a correction factor unit configured to calculate a plurality of correction factors based on the plurality of first material density values, wherein each correction factor is assigned to a second material density value, among a plurality of second material density values, for a second substance type;

an imaging unit configured to calculate CT images based on the plurality of first material density values and the plurality of second material density values, wherein at least one of the CT images is corrected via the plurality of correction factors; and a computer system configured to perform at least one of outputting or displaying the CT images corrected via the plurality of correction factors.

22. A diagnostic facility configured to assess CT images, said diagnostic facility comprising the apparatus as claimed in claim 21.

23. A control facility for a CT system, said control facility comprising the apparatus as claimed in claim 21.

24. A CT system comprising a dual-energy CT scanner, multi-energy CT scanner or photon-counting CT scanner and the control facility as claimed in claim 23.

25. An apparatus for correcting material-induced effects in CT images, the apparatus comprising:

at least one processor; and a memory storing computer-executable instructions that, when executed by the at least one processor, cause the apparatus to receive a CT scan dataset including CT scan data of an object at at least two different energies, calculate a plurality of first material density values for a first substance type based on the CT scan data of the CT scan dataset, the plurality of first material density values being spatially resolved material density values;

calculate a plurality of correction factors based on the plurality of first material density values, wherein each correction factor is assigned to a second material density value, among a plurality of second material density values, for a second substance type, and calculate CT images based on the plurality of first material density values and the plurality of second material density values, wherein at least one of the CT images is corrected via the plurality of correction factors.

* * * * *